United States Patent

Fischer et al.

[11] Patent Number: 5,905,170
[45] Date of Patent: May 18, 1999

[54] PROCESS FOR THE PRODUCTION OF 1-AMINO-1-METHYL-3(4)-AMINOMETHYLCYCLOHEXANE

[75] Inventors: Konrad Fischer, Odenthal; Oswald Wilmes, Köln; Dieter Arlt, Lemgo; Carl Casser, Köln, all of Germany; Peter Maas, Puth, Netherlands; Pierre Woestenborghs, Dilsen, Belgium; Theo Van der Knaap, Grevenbicht, Netherlands

[73] Assignee: Bayer Aktiengesellschaft, Leverkusen, Germany

[21] Appl. No.: 09/038,636

[22] Filed: Mar. 11, 1998

[30] Foreign Application Priority Data

Mar. 20, 1997 [DE] Germany ............................ 197 11 549

[51] Int. Cl.⁶ .................................................. C07C 209/36
[52] U.S. Cl. ............................................ 564/461; 564/448
[58] Field of Search ..................................... 564/461, 462, 564/448, 445

[56] References Cited

U.S. PATENT DOCUMENTS 4,613,686  9/1986  König et al. ............................ 560/335
5,449,811  9/1995  Arit ........................................ 558/431

*Primary Examiner*—Brian M. Burn
*Attorney, Agent, or Firm*—Joseph C. Gil; Thomas W. Roy

[57] ABSTRACT

The present invention relates to a process for the production of 1-amino-1-methyl-3(4)-aminomethylcyclohexane by a) simultaneously reacting 4(5)-aminomethyl-1-methylcyclohexene (CMA), hydrocyanic acid and aqueous sulphuric acid at temperatures of 60° C. to 120° C., preferably 80° C. to 120° C. to form 1-formamido-1-methyl-3(4)-aminomethylcyclohexane (FMA) in a first stage, b) adding water and hydrolyzing 1-formamido-1-methyl-3 (4)-aminomethylcyclohexane (FMA) and unreacted hydrocyanic acid in a second stage and c) adding a base and isolating 1-amino-1-methyl-3 (4)-aminomethylcyclohexane (AMCA) by extraction from the reaction mixture obtained in the second stage of the reaction, optionally after removing of formic acid.

20 Claims, No Drawings

PROCESS FOR THE PRODUCTION OF 1-AMINO-1-METHYL-3(4)-AMINOMETHYLCYCLOHEXANE

BACKGROUND OF THE INVENTION

1. Field of the Invention

The present invention relates to a process for the production of 1-amino-1-methyl-3(4)-aminomethylcyclohexane (AMCA), the precursor for the production of 1-isocyanato-1-methyl-3(4)-isocyanatomethylcyclohexane (IMCI).

2. Description of the Prior Art

DE-A 4,401,929 describes a process for the production of 1-amino-1-methyl-3(4)-aminomethylcyclohexane (AMCA) that may be illustrated by the following reaction scheme:

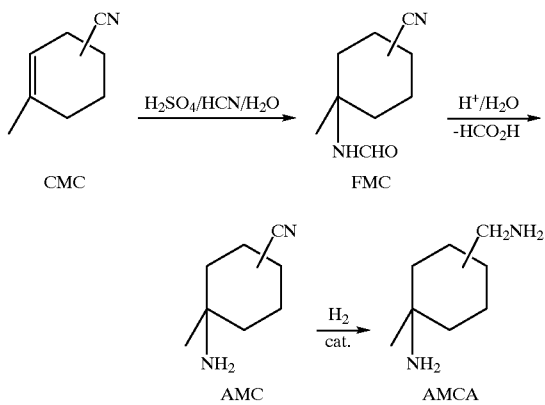

According to this reaction mechanism, 4(5)-cyano-1-methylcyclohexene (CMC) serving as starting product is caused to react with hydrocyanic acid in the presence of sulphuric acid in a Ritter reaction to form 1-formamido-1-methyl-3(4)-cyanocyclohexane (FMC). In a further reaction step the 1-formamido-1-methyl-3(4)-cyanocyclohexane (FMC) is hydrolyzed in the acidic state to form 1-amino-1-methyl-3(4)-cyanocyclohexane (AMC), which is then hydrated to form 1-amino-1-methyl-3(4)-aminomethylcyclohexane (AMCA). In order to obtain high selectivities for the formation of FMC during the Ritter reaction, a considerable excess of hydrocyanic acid is required, which means that this process can only be operated only with considerable safety measures.

European patent application EP-A 0,153,561 describes a process for the production of 1-amino-1-methyl-3(4)-aminomethylcyclohexane (AMCA) by the following reaction scheme:

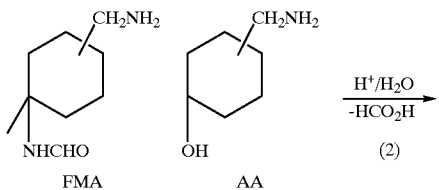

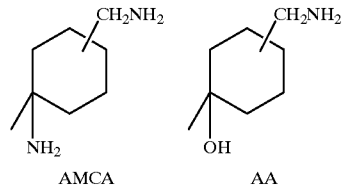

In this process the Ritter reaction (1) is carried out by introducing 4(5)-aminomethyl-1-methylcyclohexene (CMA) into sulphuric acid and then charging hydrocyanic acid to this reaction mixture at 10° to 50° C. Even after four hours about 13% of 3(4)-aminomethyl-1-methylcyclohexanol (AA) is obtained which can only be separated by distillation from the 1-amino-1-methyl-3(4)-aminomethylcyclohexane (AMCA) with difficulty (see Example 1a from EP-A 0,153,561). For the subsequent hydrolysis reaction (2), reaction-times of three hours are required in accordance with the described process. Because of the long reaction-times that are required for the Ritter reaction (1) and hydrolysis reaction (2), this process is associated with considerable investment and energy costs.

In European Patent EP-A 0,153,561, it is also possible to use 3(4)-aminomethyl-1-methylcyclohexanol (M) as the starting material for the Ritter reaction (1). However, the selectivity achieved in this case is only about 75%. Consequently an overall selectivity of about 81% is obtained in accordance with EP-A 0,153,561.

It is an object of the present invention to provide a process for the production of 1-amino-1-methyl-3(4)-aminomethylcyclohexane (AMCA) from 4(5)-aminomethyl-1-methylcyclohexene (CMA) in which short reaction-times and high selectivities are achieved and in which clear economic advantages are obtained in comparison with the previously described processes.

This object may be achieved in accordance with the process of the present invention which is described hereinafter.

SUMMARY OF THE INVENTION

The present invention relates to a process for the production of 1-amino-1-methyl-3(4)-aminomethylcyclohexane by a) simultaneously reacting 4(5)-aminomethyl-1-methylcyclohexene (CMA), hydrocyanic acid and aqueous sulphuric acid at temperatures of 60° C. to 120° C., preferably 80° C. to 120° C. to form 1-formamido-1-methyl-3(4)-aminomethylcyclohexane (FMA) in a first stage, b) adding water and hydrolyzing 1-formamido-1-methyl-3(4)-aminomethylcyclohexane (FMA) and unreacted hydrocyanic acid in a second stage and c) adding a base and isolating 1-amino-1-methyl-3(4)-aminomethylcyclohexane (AMCA) by extraction from the reaction mixture obtained in the second stage of the reaction, optionally after removing of formic acid.

DETAILED DESCRIPTION OF THE INVENTION

In the first stage of the process according to the invention 1 to 3 moles of hydrocyanic acid, preferably 1.1 to 1.7 moles of hydrocyanic acid, and two to three moles of sulphuric acid, preferably 2.2 to 2.7 moles of sulphuric acid are added per mole of CMA. The water content of the sulphuric acid is adjusted such that the molar ratio of CMA to water is 1:7 to 1:2, preferably 1:6 to 1:3.

In the process according to the invention the reaction times required for a conversion of greater than 99% amount are 3 to 60 minutes for the first stage of the reaction. The high temperatures and excesses of hydrocyanic acid and sulphuric acid accelerate the reaction.

The first stage of the reaction can be carried out either discontinuously in an agitator vessel or continuously, preferably continuously. A continuous reaction can be carried out in a cascade of agitator vessels, in a loop reactor or in a tubular reactor and also in any series connection of these types of reactors. Preferred is a combination of a loop reactor with a tube reactor, since this combination enables the heat of reaction to be dissipated in particularly favorable manner.

The fact that high yields are achieved in the first stage of the reaction is surprising, since at the process temperatures according to the invention it would be expected that hydrocyanic acid would hydrolyze to form ammonium formate. Furthermore, it is also surprising that selectivities greater than 95% are achieved by simultaneously adding the starting components (CMA, hydrocyanic acid and aqueous sulphuric acid) at the temperatures according to the invention of 60° C. to 120° C., preferably 80° C. to 120° C. If the addition of the starting components at the temperatures according to the invention were to be effected in the manner described in EP-A 0,153,561, then distinctly lower selectivities would be expected, since 3(4)-amino-methyl-1-methylcyclohexanol (AA) would be eliminated by the intermolecular dimerization of the desired Ritter reaction.

In the second stage of the process according to the invention the 1-formamido-1-methyl-3(4)-aminomethylcyclohexane that is formed in the first stage and excess hydrocyanic acid is hydrolyzed. For this reaction water is added such that the concentration of sulphuric acid in the reaction mixture is 35 to 60 wt-%, preferably 35 to 45 wt-%. The hydrolysis is carried out at a temperature of 80° C. to 120° C. The second stage can be carried out either discontinuously or continuously, for example, in a cascade of agitator vessels or in a tube reactor.

Isolation of 1-amino-1-methyl-3(4)-aminomethylcyclohexane (AMCA) from the reaction mixture obtained after hydrolysis is carried out by extraction. Prior to extraction the reaction mixture obtained after hydrolysis is made alkaline by the addition of a base. Suitable bases include an aqueous ammonia solution, alkali metal hydroxides (such as sodium hydroxide) and/or alkaline earth metal hydroxides. The aqueous ammonia solution is added in such a quantity that the reaction mixture has an ammonia concentration of 6% to 20%, an AMCA concentration of 8% to 15% and an ammonium sulphate concentration of 10% to 30%.

The quantity and the water content of the alkali metal and alkaline earth metal hydroxides, in particular sodium hydroxide, that may be used for neutralization are selected such that the reaction mixture has a pH of 10 to 14, preferably 12 to 14, a (sodium) sulphate concentration of 10% to 25% and an AMCA concentration of 5% to 15%.

Suitable extracting agents for the extraction of AMCA include chlorinated hydrocarbons such as dichloromethane or chlorobenzene; hydrocarbons such as toluene or xylene; ethers such as tert-butyl methyl ether; esters such as ethyl acetate or n-butyl acetate; ketones such as methyl isobutyl ketone or methyl tert-butyl ketone; alcohols such as n-butanol, isobutanol, 1-pentanol, 2-methyl-1-butanol, 2-methyl-4-pentanol or cyclohexanol; and mixtures of these solvents. Toluene, isobutanol, cyclohexanol and 2-methyl-4-pentanol are particularly preferred.

Prior to isolation of the AMCA, it is preferred to remove the formic acid that is present in the reaction mixture after hydrolysis of 1-formamido-1-methyl-3(4)-aminomethylcyclohexane (FMA) and the excess hydrocyanic acid. Removal of formic acid is especially preferred when valuable products, such as ammonium sulphate or sodium sulphate, are to be isolated in pure form from the salt solution remaining after extraction of the AMCA. Separation of formic acid carried out by extraction. The pH is adjusted to a value of 1.3 to 3.0 by the addition of ammonia or sodium hydroxide. Suitable extracting agents for the extraction include alcohols such as isobutanol, cyclohexanol and 2-methyl-4-pentanol.

The salt solutions remaining after extraction of AMCA may be processed by suitable means into useful substances. For example, the salt solution containing sodium sulphate and, optionally, sodium formate may be subjected to electrolysis and the resulting sulphuric acid and caustic-soda solution may be recirculated, optionally after concentration, into the reaction process. Selective crystallization of sodium sulphate from the salt solution containing sodium sulphate and sodium formate is also possible. The salt solution containing ammonium sulphate and, optionally, ammonium formate may be subjected to thermolytic decomposition, accompanied by liberation of sulphur dioxide that can be recycled for the production of sulphuric acid. It is also possible to isolate ammonium sulphate in pure form as a valuable product by crystallization.

The AMCA obtained by the process according to the invention may, after removal of the extracting agent, may optionally be phosgenated in known manner to form IMCI.

In the following examples all percentages are percentages by weight.

EXAMPLES

1. Ritter Reaction

4(5)-aminomethyl-1-methylcyclohexene (CMA), hydrocyanic acid and aqueous sulphuric acid were pumped continuously in an agitator vessel (155 ml) with overflow. After 60 minutes, selectivities and conversion were determined in the overflow by means of HPLC. The results for the various examples are set forth in Table 1.

TABLE 1

| Ex. | CMA | | HCN | | Sulphuric acid 70% | | Sulphuric acid 75% | | Sulphuric acid 80% | | Total flow | |
|---|---|---|---|---|---|---|---|---|---|---|---|---|
| No. | ml/min | g/min | ml/min | g/min | ml/min | g/min | ml/min | g/min | ml/min | g/min | ml/min | g/min |
| 1 | 3.42 | 3.04 | 1.20 | 0.85 | | | 5.71 | 9.45 | | | 10.33 | 13.43 |

TABLE 1-continued

| | | | | | | | | | | |
|---|---|---|---|---|---|---|---|---|---|---|
| 2 | 3.42 | 3.04 | 1.20 | 0.85 | | 5.71 | 9.54 | | | 10.33 | 13.43 |
| 3 | 3.42 | 3.04 | 1.20 | 0.85 | | 5.71 | 9.54 | | | 10.33 | 13.43 |
| 4 | 6.84 | 6.09 | 2.41 | 1.71 | | 11.41 | 19.07 | | | 20.67 | 26.87 |
| 5 | 6.84 | 6.09 | 2.41 | 1.17 | | 11.42 | 19.07 | | | 20.67 | 26.87 |
| 6 | 7.53 | 6.70 | 2.65 | 1.88 | | 10.49 | 17.52 | | | 20.67 | 26.10 |
| 7 | 8.02 | 7.14 | 2.82 | 2.00 | | 9.83 | 16.42 | | | 20.67 | 25.56 |
| 8 | 8.38 | 7.46 | 2.95 | 2.09 | | 9.34 | 15.60 | | | 20.67 | 25.15 |
| 9 | 5.13 | 4.57 | 1.80 | 1.28 | | 8.57 | 14.31 | | | 15.50 | 20.16 |
| 10 | 7.91 | 7.04 | 2.78 | 1.97 | | | | 9.97 | 17.25 | 29.66 | 26.26 |
| 11 | 7.68 | 6.84 | 2.29 | 1.63 | | 10.70 | 17.87 | | | 20.67 | 26.33 |
| 12 | 7.53 | 6.70 | 2.65 | 1.88 | | 10.49 | 17.52 | | | 20.67 | 26.10 |

| | | Dwell | Analyses | | | | Conversion | | Selectivity FMA + |
|---|---|---|---|---|---|---|---|---|---|
| Test No. | Temp. °C. | time min | AA wt-% | FMA wt-% | AMCA wt-% | CMA wt-% | AA % | CMA % | AMCA % |
| 1 | 80 | 15.00 | 0.13 | 28.00 | 2.20 | 0.00 | 99 | 100 | 99 |
| 2 | 100 | 15.00 | 0.00 | 25.00 | 4.75 | 0.00 | 100 | 100 | 99 |
| 3 | 117 | 15.00 | 0.13 | 19.33 | 9.48 | 0.00 | 99 | 100 | 100 |
| 4 | 101 | 7.50 | 0.84 | 27.50 | 1.90 | 0.00 | 97 | 100 | 99 |
| 5 | 87 | 7.50 | 1.93 | 27.00 | 1.06 | 0.00 | 93 | 100 | 99 |
| 6 | 100 | 7.50 | 1.40 | 29.21 | 2.84 | 0.00 | 95 | 100 | 98 |
| 7 | 100 | 7.50 | 2.35 | 30.10 | 3.49 | 0.00 | 93 | 100 | 97 |
| 8 | 100 | 7.50 | 3.37 | 31.73 | 3.53 | 0.00 | 90 | 100 | 99 |
| 9 | 100 | 10.00 | 0.21 | 27.52 | 2.50 | 0.00 | 99 | 100 | 100 |
| 10 | 104 | 7.50 | 0.00 | 33.86 | 1.33 | 0.00 | 100 | 100 | 97 |
| 11 | 67 | 7.50 | 5.95 | 27.13 | 0.36 | 0.00 | 80 | 100 | 98 |
| 12 | 65 | 7.50 | 0.00 | 33.21 | 1.00 | 0.00 | 100 | 100 | 99 |

| | | | | | Addition rate | | | | | | |
|---|---|---|---|---|---|---|---|---|---|---|---|
| Ex. | CMA | | HCN | | Sulphuric acid 70% | | Sulphuric acid 75% | | Sulphuric acid 80% | | Total flow |
| No. | ml/min | g/min | ml/min | g/min | ml/min | g/min | ml/min | g/min | ml/min | g/min | ml/min | g/min |
| 13 | 7.68 | 6.84 | 2.29 | 1.63 | | | 10.70 | 17.87 | | | 20.67 | 26.33 |
| 14 | 9.59 | 8.54 | 2.90 | 2.06 | | | 13.35 | 22.29 | | | 25.84 | 32.89 |
| 15 | 9.60 | 8.54 | 2.90 | 2.06 | | | 13.35 | 22.29 | | | 25.85 | 32.90 |
| 16 | 9.60 | 8.54 | 2.90 | 2.06 | | | 13.35 | 22.29 | | | 25.85 | 32.90 |
| 17 | 6.43 | 5.72 | 1.91 | 1.36 | | | 7.15 | 11.94 | | | 15.49 | 19.02 |
| 18 | 4.91 | 4.37 | 1.46 | 1.04 | 9.12 | 14.68 | | | | | 15.49 | 20.09 |
| 19 | 5.45 | 4.85 | 1.62 | 1.15 | 8.38 | 13.49 | | | | | 15.45 | 19.49 |
| 20 | 5.83 | 5.19 | 1.74 | 1.24 | 7.90 | 12.72 | | | | | 15.47 | 19.14 |
| 21 | 6.48 | 5.77 | 0.00 | 0.00 | | | 9.02 | 15.06 | | | 15.50 | 20.83 |
| 22 | 6.48 | 5.77 | 0.00 | 0.00 | | | 9.02 | 15.06 | | | 15.50 | 20.83 |
| 23 | 6.48 | 5.77 | 0.00 | 0.00 | | | 9.02 | 15.06 | | | 15.50 | 20.83 |

| | | Dwell | Analyses | | | | Conversion | | Selectivity FMA + |
|---|---|---|---|---|---|---|---|---|---|
| Test No. | Temp. °C. | time min | AA wt-% | FMA wt-% | AMCA wt-% | CMA wt-% | AA % | CMA % | AMCA % |
| 13 | 84 | 7.50 | 2.63 | 31.15 | 0.91 | 0.00 | 91 | 100 | 100 |
| 14 | 71 | 6.00 | 7.18 | 26.35 | 0.23 | 0.00 | 76 | 100 | 99 |
| 15 | 80 | 6.00 | 3.47 | 30.55 | 0.48 | 0.00 | 88 | 100 | 100 |
| 16 | 90 | 6.00 | 2.33 | 30.50 | 1.53 | 0.00 | 92 | 100 | 99 |
| 17 | 84 | 10.01 | 6.45 | 29.00 | 1.85 | 2.35 | 83 | 92 | 99 |
| 18 | 90 | 10.01 | 1.78 | 24.50 | 2.17 | 0.00 | 93 | 100 | 99 |
| 19 | 90 | 10.03 | 3.77 | 25.00 | 2.55 | 0.60 | 86 | 98 | 98 |
| 20 | 90 | 10.02 | 4.99 | 24.50 | 3.02 | 1.45 | 83 | 95 | 97 |
| 21 | 82 | 10.00 | 22.30 | 0.00 | 0.00 | 0.00 | 30 | 100 | a) |
| 22 | 97 | 10.00 | 14.10 | 0.00 | 0.00 | 0.00 | 56 | 100 | a) |
| 23 | 112 | 10.00 | 9.04 | 0.00 | 0.00 | 0.00 | 72 | 100 | a) | a) In the GC-MS spectrum a large number of compounds having a mass of 268 (=2×AA.H$_2$O) were identified. These tests prove that when adding the starting components at the temperatures according to the present invention using the sequence of addition described in EP-A 0 153 561, the 3(4)-aminomethyl-1-methylcyclohexanol (AA) arising primarily in this case is eliminated by intermolecular dimerization of the desired Ritter reaction. Therefore, when compared to the method of addition the starting components according to the present invention, distinctly lower selectivities are obtained according to the European application.

2. Hydrolysis Reaction

A mixture containing of 45% sulphuric acid, 22.4% water, 11.7% AMCA, 16.8% FMA and 0.06% hydrocyanic acid was heated for 30 minutes to 110° C. Analysis of the reaction mixture by HPLC yielded an AMCA content of 24.84%, an FMA content of 0.4% and a hydrocyanic acid content of 3.8 ppm. This corresponds to an FMA conversion of 98% and an AMCA selectivity of 96%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of 1-amino-1-methyl-3(4)-aminomethylcyclohexane (AMCA) which comprises
    a) simultaneously reacting 4(5)-aminomethyl-1-methylcyclohexene (CMA), hydrocyanic acid and aqueous sulphuric acid at temperatures of 60° C. to 120° C. to form 1-formamido-1-methyl-3(4)-aminomethylcyclohexane (FMA) in a first stage,
    b) adding water and hydrolyzing 1-formamido-1-methyl-3(4)-aminomethylcyclohexane (FMA) and unreacted hydrocyanic acid in a second stage and
    c) adding a base and isolating 1-amino-1-methyl-3(4)-aminomethylcyclohexane (AMCA) by extraction from the reaction mixture obtained in the second stage of the reaction, optionally after removing of formic acid.

2. The process of claim 1 wherein 1 to 3 moles of hydrocyanic acid 2 to 3 moles of sulphuric acid are introduced per mole of CMA, and the water content of the sulphuric acid is adjusted such that the molar ratio of CMA to water is 1:2 to 1:7.

3. The process of claim 1 wherein an aqueous ammonia solution is used as the base in step c) and the aqueous ammonia solution is used in an amount such that the ammonia concentration is 6% to 20%, the AMCA concentration is 8% to 15% and the ammonium sulphate concentration is 10% to 30%.

4. The process of claim 2 wherein an aqueous ammonia solution is used as the base in step c) and the aqueous ammonia solution is used in an amount such that the ammonia concentration is 6% to 20%, the AMCA concentration is 8% to 15% and the ammonium sulphate concentration is 10% to 30%.

5. The process of claim 1 wherein water is present in step b) in an amount such that the concentration of sulphuric acid is 35 to 60 wt-%.

6. The process of claim 2 wherein water is present in step b) in an amount such that the concentration of sulphuric acid is 35 to 60 wt-%.

7. The process of claim 3 wherein water is present in step b) in an amount such that the concentration of sulphuric acid is 35 to 60 wt-%.

8. The process of claim 4 wherein water is present in step b) in an amount such that the concentration of sulphuric acid is 35 to 60 wt-%.

9. The process of claim 1 wherein AMCA is isolated using 2-methyl-4-pentanol as the extracting agent.

10. The process of claim 1 wherein all of the process steps are carried out continuously.

11. A process for the production of 1-amino-1-methyl-3(4)-aminomethylcyclohexane (AMCA) which comprises
    a) simultaneously reacting 4(5)-aminomethyl-1-methylcyclohexene (CMA), hydrocyanic acid and aqueous sulphuric acid at temperatures of 80° C. to 120° C. to form 1-formamido-1-methyl-3(4)-aminomethylcyclohexane (FMA) in a first stage,
    b) adding water and hydrolyzing 1-formamido-1-methyl-3(4)-aminomethylcyclohexane (FMA) and unreacted hydrocyanic acid in a second stage and
    c) adding a base and isolating 1-amino-1-methyl-3(4)-aminomethylcyclohexane (AMCA) by extraction from the reaction mixture obtained in the second stage of the reaction, optionally after removing of formic acid.

12. The process of claim 11 wherein 1.1 to 1.7 moles of hydrocyanic acid 2.2 to 2.7 moles of sulphuric acid are introduced per mole of CMA, and the water content of the sulphuric acid is adjusted such that the molar ratio of CMA to water is 1:3 to 1:6.

13. The process of claim 11 wherein an aqueous ammonia solution is used as the base in step c) and the aqueous ammonia solution is used in an amount such that the ammonia concentration is 6% to 20%, the AMCA concentration is 8% to 15% and the ammonium sulphate concentration is 10% to 30%.

14. The process of claim 12 wherein an aqueous ammonia solution is used as the base in step c) and the aqueous ammonia solution is used in an amount such that the ammonia concentration is 6% to 20%, the AMCA concentration is 8% to 15% and the ammonium sulphate concentration is 10% to 30%.

15. The process of claim 11 wherein water is present in step b) in an amount such that the concentration of sulphuric acid is 35 to 45 wt-%.

16. The process of claim 12 wherein water is present in step b) in an amount such that the concentration of sulphuric acid is 35 to 45 wt-%.

17. The process of claim 13 wherein water is present in step b) in an amount such that the concentration of sulphuric acid is 35 to 45 wt-%.

18. The process of claim 14 wherein water is present in step b) in an amount such that the concentration of sulphuric acid is 35 to 45 wt-%.

19. The process of claim 11 wherein AMCA is isolated using 2-methyl-4-pentanol as the extracting agent.

20. The process of claim 11 wherein all of the process steps are carried out continuously.

* * * * *